(12) United States Patent
Camden

(10) Patent No.: US 6,258,831 B1
(45) Date of Patent: Jul. 10, 2001

(54) VIRAL TREATMENT

(75) Inventor: James Berger Camden, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/535,172

(22) Filed: Mar. 27, 2000

Related U.S. Application Data

(63) Continuation-in-part of application No. 09/281,896, filed on Mar. 31, 1999, now abandoned.

(51) Int. Cl.$^7$ .................................................. A61K 31/433
(52) U.S. Cl. ............................................................ 514/361
(58) Field of Search ...................................... 514/363, 361

(56) References Cited

U.S. PATENT DOCUMENTS 5,376,670 * 12/1994 Connor et al. ....................... 514/383

FOREIGN PATENT DOCUMENTS

| 0 540 143 A2 | 5/1993 | (EP) . |
| WO 99/45027 | 9/1999 | (WO) . |

OTHER PUBLICATIONS

Khare et al., Indian J. Chem.,Section B: Org. Chem., 34B(9), 828–31 (abstract), 1995.*

Kurzer, et al., *J. Chem. Soc. Perkin Trans.,* 1985, vol. 1(2), pp. 311–314.

Kurzer, et al., *J. Herterocyclic Chem.,* 1989, vol. 26(2), pp. 355–360.

Schoeb et al.—"Studies in Possible Oral Hypoglycemic Agents, Part III. Synthesis of Some 3–Amino–5–Phenyl and 5–Amino–3–Methyl–1,2,4–Thiadiazole Derivatives", J. Indian Chem Soc., vol. 40, No. 5, 1963, pp. 369–372, XP000957483.

* cited by examiner

*Primary Examiner*—Phyllis G. Spivack
(74) *Attorney, Agent, or Firm*—Rose Ann Dabek; Steven W. Miller

(57) ABSTRACT

Methods are disclosed to treat viral infections, particularly hepatitis C, herpes simplex, Kaposi's sarcoma and HIV, comprising administrating a (5-aryl-1,2,4-thiadiazol)-3-yl thiourea derivative or (5-aryl-1,2,4-thiadiazol)-3-yl urea derivative of the formula:

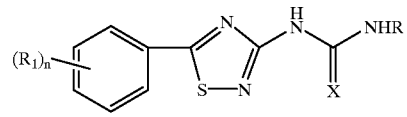

wherein X is oxygen or sulfur, R is hydrogen or alkyl having from 1–3 carbons, n is 0–4, $R_1$ is independently selected from the group consisting of hydrogen, alkyl having from 1 to 7 carbon atoms, chloro, bromo or fluoro, oxychloro, alkoxy having the formula —$O(CH_2)_y CH_3$ wherein y is from 1 to 6, or a pharmaceutically acceptable acid addition salt or prodrug thereof. The preferred compound is (5-phenyl-1,2,4-thiadiazol-3-yl) thiourea.

32 Claims, No Drawings

VIRAL TREATMENT

This application is a continuation in part of application of J. B. Camden, Ser. No. 09/281,896 filed Mar. 31, 1999 abandoned.

TECHNICAL FIELD

This invention is a pharmaceutical composition that is effective against the treatment of viruses. The composition can be used to treat viral infections, notably hepatitis, including hepatitis C virus (HCV) hepatitis B virus (HBV), human immunodeficiency syndrome (HIV), and Kaposi sarcoma (HHV8). The composition comprises one or more (5-aryl-1,2,4-thiadiazol)-3-yl- urea or (5-aryl-1,2,4-thiadiazol)-3-yl thiourea derivatives. Method of treating viral infections are also disclosed.

BACKGROUND OF THE INVENTION

HIV and other viral infections such as hepatitis are a few of the leading causes of death. HIV is the virus known to cause acquired immunodeficiency syndrome (AIDS) in humans. HIV is a disease in which a virus is replicated in the body or in host cells. The virus attacks the body's immune system.

Several drugs have been approved for treatment of this devastating disease, including azidovudine (AZT), didanosine (dideoxyinosine, ddI), d4T, zalcitabine (dideoxycytosine, ddC), nevirapine, lamivudine (epivir, 3TC), saquinavir (Invirase), ritonavir (Norvir), indinavir (Crixivan), and delavirdine (Rescriptor). See M. I. Johnston & D. F. Hoth, Science, 260(5112), 1286–1293 (1993) and D. D. Richman, Science, 272(5270), 1886–1888 (1996). An AIDS vaccine (Salk's vaccine) has been tested and several proteins which are chemokines from CD8 have been discovered to act as HIV suppressors. In addition to the above synthetic nucleoside analogs, proteins, and antibodies, several plants and substances derived from plants have been found to have in vitro anti-HIV activity. However, HIV virus is not easily destroyed nor is there a good mechanism for keeping the host cells from replicating the virus.

Thus, medical professionals continue to search for drugs that can prevent HIV infections, treat HIV carriers to prevent their disease from progressing to full-blown deadly AIDS, and to treat the AIDS patient.

Herpes simplex virus (HSV) types 1 and 2 are persistent viruses that commonly infect humans; they cause a variety of troubling human diseases. HSV type 1 causes oral "fever blisters" (recurrent herpes labialis), and HSV type 2 causes genital herpes, which has become a major venereal disease in many parts of the world. No fully satisfactory treatment for genital herpes currently exists. In addition, although it is uncommon, HSV can also cause encephalitis, a life-threatening infection of the brain. (The Merck Manual, Holvey, Ed., 1972; Whitley, Herpes Simplex Viruses, In: Virology, 2nd Ed., Raven Press (1990)). A most serious HSV-caused disorder is dendritic keratitis, an eye infection that produces a branched lesion of the cornea, which can in turn lead to permanent scarring and loss of vision. Ocular infections with HSV are a major cause of blindness. HSV is also a virus which is difficult, if not impossible to cure.

Hepatitis is a disease of the human liver. It is manifested with inflammation of the liver and is usually caused by viral infections and sometimes from toxic agents. Hepatitis may progress to liver cirrhosis, liver cancer, and eventually death. Several viruses such as hepatitis A, B, C, D, E and G are known to cause various types of viral hepatitis. Among them, HBV and HCV are the most serious. HBV is a DNA virus with avirion size of 42 nm. HCV is a RNA virus with a virion size of 30–60 nm. See D. S. Chen, J. Formos. Med. Assoc., 95(1), 6–12 (1996).

Hepatitis C infects 4 to 5 times the number of people infected with HIV. Hepatitis C is difficult to treat and it is estimated that there are 500 million people infected with it worldwide (about 15 time those infected with HIV). No effective immunization is currently available, and hepatitis C can only be controlled by other preventive measures such as improvement in hygiene and sanitary conditions and interrupting the route of transmission. At present, the only acceptable treatment for chronic hepatitis C is interferon which requires at least six (6) months of treatment and or ribavarin which can inhibit viral replication in infected cells and also improve liver function in some people. Treatment with interferon however has limited long term efficacy with a response rate about 25%.

Hepatitis B virus infection can lead to a wide spectrum of liver injury. Moreover, chronic hepatitis B infection has been linked to the subsequent development of hepatocellular carcinoma, a major cause of death. Current prevention of HBV infection is a hepatitis B vaccination which is safe and effective. However, vaccination is not effective in treating those already infected (i.e., carriers and patients). Many drugs have been used in treating chronic hepatitis B and none have been proven to be effective, except interferon.

Treatment of HCV and HBV with interferon has limited success and has frequently been associated with adverse side effects such as fatigue, fever, chills, headache, myalgias, arthralgias, mild alopecia, psychiatric effects and associated disorders, autoimmune phenomena and associated disorders and thyroid dysfunction.

Because the interferon therapy has limited efficacy and frequent adverse effects, a more effective regimen is needed.

In the present invention it has been discovered that the compounds described above are useful for the treatment of hepatitis C virus, hepatitis B virus, herpes simplex and the treatment of HIV infection and other viral infections.

SUMMARY OF THE INVENTION

A pharmaceutical composition for administering to treating animals, and in particular, warm blooded animals and humans, infected with a virus. The composition comprises a therapeutically effective amount of an anti-viral compound and optionally a pharmaceutical carrier. The anti-viral compound is selected from the group consisting of (5-aryl-1,2,4-thiadiazol)-3-yl thiourea derivatives or (5-aryl-1,2,4-thiadiazol)-3-yl urea derivatives having the formula:

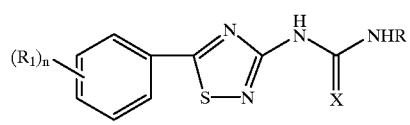

wherein X is oxygen or sulfur, R is hydrogen or alkyl having from 1–3 carbons, n is 0–4, $R_1$ is independently selected from the group consisting of hydrogen, alkyl having from 1 to 7 carbon atoms, chloro, bromo or fluoro, oxychloro, alkoxy having the formula —$O(CH_2)_yCH_3$ wherein y is from 1 to 6 or a pharmaceutical addition salt or prodrug thereof.

Preferred anti-viral compositions comprise a therapeutically effective amount of the anti-viral compound (5-phenyl-1,2,4-thiadiazol)-3-yl thiourea (5-phenyl-3-thioureido-1,2,4-thiadiazole), which has the formula:

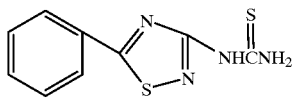

The compositions can be used to treat hepatitis C, hepatitis B, herpes simplex and other viral infections.

More specifically, this invention provides an anti-viral composition comprising a pharmaceutical carrier and a (5-aryl-1,2,4-thiadiazol)-3-yl thiourea derivative or (5-aryl-1,2,4-thiadiazol)-3-yl urea derivative as defined herein along with a method for treating viral infections for example, hepatitis C, hepatitis B. other hepatitis infections, HIV, influenza, and rhinoviruses, Kaposi's sarcoma, virus herpes simplex, and the like. The (5-aryl-1,2,4-thiadiazol)-3-yl thiourea or corresponding urea derivatives are also fungicidal and can be used to treat certain fungal infections. This same composition has utility against some fungi, in particular those which are common in HIV patients. Moreover the compounds are effective in the treatment of Bovine Diarrhea Virus and can be used in veterinary treatment for such disease.

The present invention also provides methods for the treatment of HIV infection comprising administering to a host infected with HIV a pharmaceutically or therapeutically effective or acceptable amount of a compound as described above.

The present invention also comprises the use of a combination therapy in the treatment of viral infections.

The compositions can be used in conjunction with other treatments. The route of administration is the same as for other medical treatments. The drug can be given daily or from 1 to 4 times a week.

DETAILED DESCRIPTION OF THE INVENTION

A. Definitions

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention.

As used herein, the term "therapeutically effective amount" is meant an amount of a compound of the present invention effective to yield the desired therapeutic response. For example to inhibit HIV infection or treat the symptoms of infection in a host or an amount effective to treat hepatitis. The specific therapeutically effective amount will, obviously, vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, a "pharmaceutical addition salt" is a salt of the arylthiazolyl thiourea or urea which are modified by making an acid or base salt of the compounds. Examples of pharmaceutical addition salts include, but are not limited to, mineral or organic acid salt of basic residues such as amines, alkali or organic salt of acidic residues such as carboxylic acids. Preferably the salts are made using an organic or inorganic acid. These preferred acid addition salts are chlorides, bromides, sulfates, nitrates, phosphates, sulfonates, formates, tartrates, maleates, malates, citrates, benzoates, salicylates, ascorbates, and the like.

As used herein, a "pharmaceutical carrier" is a pharmaceutically acceptable solvent, suspending agent or vehicle for delivering the anti-viral agent to the animal or human. The carrier can be liquid or solid and is selected with the planned manner of administration in mind.

As used herein, the terms "anti-viral compounds" are the (5-aryl-1,2,4-thiadiazol)-3-yl thiourea derivatives or (5-aryl-1,2,4-thiadiazol)-3-yl urea derivatives and the pharmaceutical addition salts or prodrugs thereof. The preferred anti-viral compound is 5-phenyl-3-thioureido-1,2,4-thiadiazole.

As used herein, the term "(5-aryl-1,2,4-thiadiazol)-3-yl thiourea derivatives" or "(5-aryl-1,2,4-thiadiazol)-3-yl urea derivatives" or "aryl thiadiazolyl thiourea or urea derivatives" includes compounds having the formula:

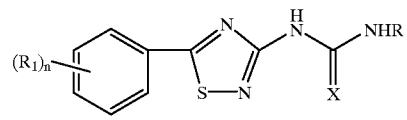

wherein X is oxygen or sulfur, R is hydrogen or alkyl having from 1–3 carbons, n is 0–4, $R_1$ is independently selected from the group consisting of hydrogen, alkyl having from 1 to 7 carbon atoms, chloro, bromo or fluoro, oxychloro, alkoxy having the formula —O(CH$_2$)YCH$_3$ wherein y is from 1 to 6 or its pharmaceutical addition salt or its prodrug.

As used herein, "Alkyl" can be any branched, straight chain or cyclic alkane or alkene generally having less than 8 carbons As used herein "Aryl" is any substituted phenyl compound and including phenyl itself wherein R is hydrogen and n is 5.

As used herein, the term "Prodrugs" are considered to be any covalently bonded carriers which release the active parent drug according to the formula of derivatives described above in vivo when such prodrug is administered to a mammalian subject or patient in need of treatment. Prodrugs of the arylthiadiazolyl thiourea or urea derivatives are prepared by modifying functional groups present in the compounds in such a way that the modifications are cleaved, either in routine manipulation or in vivo, to the parent compounds. Prodrugs include compounds wherein free hydroxyl, sulfhydryl, or amine groups are bonded to any group that, when administered to a mammalian subject, cleaves to form a free hydroxyl, amino, or sulfhydryl group, respectively. Examples of prodrugs include, but are not limited to, acetate, formate, or benzoate derivatives of alcohol and amine functional groups in the arylthiazolyl thiourea derivatives or arylthiazoloyl urea derivative; phosphate esters, dimethylglycine esters, aminoalkylbenzyl esters, aminoalkyl esters and carboxyalkyl esters of alcohol and phenol functional groups or the aminoalkylbenzyl amides, aminoalkyl amides and carboxyalkyl amides of the amino functional groups in the arylthiazolyl thiourea derivatives or arylthiazoloyl urea derivative; and the like.

As used herein "viruses" includes viruses which infect animals or mammals, including humans. Viruses includes HIV, influenza, polio viruses, herpes simplex, hepatitis B, hepatitis C and other viral strains of hepatitis, Kaposi's sarcoma, virus rhinoviruses, and the like.

As used herein "combination therapy" means that the patient in need of the drug is treated or given another drug for the disease in conjunction with the arylthiazolyl thiourea or arylthiazolyl urea derivatives. This combination therapy can be sequential therapy where the patient is treated first with one or more drugs and then the other, or two or more drugs are given simultaneously.

B. The Anti-Viral Compounds

The anti-viral material is (5-aryl-1,2,4-thiadiazol)-3-yl thiourea derivatives or (5-aryl-1,2,4-thiadiazol)-3-yl urea derivatives or their pharmaceutical addition salt or prodrugs having the formula:

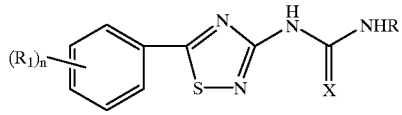

wherein X is oxygen or sulfur, R is hydrogen or alkyl having from 1–3 carbons, n is 1–4, $R_1$ is independently selected from the group consisting of hydrogen, alkyl having from 1 to 7 carbon atoms, chloro, bromo or fluoro, oxychloro, alkoxy having the formula —$O(CH_2)_yCH_3$ wherein y is from 0 to 6, preferably from 2 to 4. Preferably the (5-aryl-1,2,4-thiadiazol)-3-yl- urea or (5-aryl-1,2,4-thiadiazol)-3-yl-thiourea derivative is substituted with an alkyl of less than 4 carbons, a halogen, preferably a chloro in the 7 or 8 position and the remaining substituents of the benzene ring are hydrogen. The most preferred anti-viral is (5-phenyl-1,2,4-thiadiazol)-3-yl thiourea.

Pharmaceutical addition salt of the arylthiazolyl thiourea or arylthiazolyl urea derivatives include the conventional non-toxic salt or the quaternary ammonium salt of the arylthiazolyl thiourea or arylthiazolyl urea derivatives formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

C. Synthesis

The arylthiazolyl thiourea or arylthiazolyl urea derivatives can be prepared in a number of ways well known to one skilled in the art of organic synthesis. The arylthiazolyl thiourea or arylthiazolyl urea derivatives can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference.

The compounds can be synthesized by a desulphurization of aromatic thioureas or urea compounds using hydrogen peroxide in alkali or by reacting the corresponding 3-amino-5-aryl-1,2,4-thiadiazole with ethoxy carbonyl isothiocyanate to produce the ethoxycarbonyl-3-(5'-aryl-1',2',4'-thiadiazol-3'-yl)thiourea or 3-(5'-aryl-1',2',4-thiadiazol-3'-yl) urea which is then reacted with sodium hydroxide in ethanol and then acidified.

(5-Phenyl-1,2,4-thiadiazol)-3-yl thiourea is prepared by the method described in Kurzer, et al, *J. Chem. Soc. Perkin Trans.* 1(2), 311–314 (1985) and Kurzer, et al., *J. Heterocycl. Chem.*, 26 (2), 355–60 (1989).

(5-Phenyl-1,2,4-thiadiazol)-3-yl thiourea can also be prepared by the hydrolysis of 3-[N-benzoylthioureido]-5-phenyl-1,2,4-thiadiazole using 3 molar potassium hydroxide at about 60° C. The mixture is cooled, and then acidified with concentrated hydrochloric acid. Concentrated ammonium hydroxide is then used to basify the resultant product. The material from this hydrolysis procedure is pure (about 99%) and the yield is high.

The pharmaceutical addition salt of the present invention can be synthesized from the arylthiazolyl thiourea or arylthiazolyl urea derivatives which contain a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference. The disclosures of all of the references cited herein are hereby incorporated herein by reference in their entirety.

D. Dosage

The compounds can be administered in one dose, continuously or intermittently throughout the course of treatment. Methods of determining the most effective means and dosage of administration are well known to those of skill in the art. The compounds can be administered in one dose, continuously or intermittently throughout the course of treatment. The compounds may also be given daily or from 1 to 4 times a week. The compounds of the present invention can be given in one or more doses on a daily basis or from one to three times a week. Twice weekly dosing over a period of at least several weeks is preferred. Often the anti-viral compounds will be administered for extended periods of time and may be administered for the lifetime of the patient. Methods of determining the most effective means and dosage of administration are well known to those of skill in the art. Single or multiple administrations can be carried out with one dose level and pattern being selected by the administrator.

The compounds are generally safe. The oral $LD_{50}$ is greater than 6000 mg/kg in mice and there are no special handling requirements. By way of general guidance, a dosage of as little as about 1 milligrams (mg) per kilogram (kg) of body weight and preferably as little as 10 mg/kg and up to about 10,000 mg per kg of body weight is suitable. Preferably from 10 mg/kg to about 5000 mg/kg of body weight is used. Most preferably the doses are between 250 mg/kg to about 5000 mg/kg. Generally, the dosage in man is lower than for small warm blooded mammals such as mice. By way of guidance the human dose is about $\frac{1}{12}$ that of mice. Thus, if 25 mg/kg is effective in mice, a dose of 2 mg/kg would be used for a 60 kg person, and a typical dosage would be 120 mg.

The dosage administered will, of course, vary depending upon known factors, such as the pharmacodynamic characteristics of the particular agent and its mode and route of administration; the age, health and/or weight of the recipient; the nature and extent of the symptoms; the kind of concurrent treatment; the frequency of treatment; and the effect desired.

E. Method of Administering and Dosage Delivery Forms

The compounds of the present invention can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical or injection into or around the virus.

The dosage amounts are based on the effective inhibitory concentrations observed in anti-viral studies. The preferred route will vary with the (1) condition and age of the recipient, (2) virus and being treated (3) nature of the infection and (4) desired blood levels. It is believed that parenteral treatment by intravenous, subcutaneous, or intramuscular application of the compounds of the present invention formulated with an appropriate carrier, other antiviral agents or compounds or diluents to facilitate application will be the preferred method of administering the compounds to warm blooded animals.

The (5-aryl-1,2,4-thiadiazol)-3-yl thiourea derivatives or (5-aryl-1,2,4-thiadiazol)-3-yl urea derivatives are preferably micronized or powdered so that it is more easily dispersed and solubilized by the body. Processes for grinding or pulverizing drugs are well known in the art. For example, a hammer mill or similar milling device can be used. The preferred particle size is less than about 100µ and preferably less than 50µ. These compounds are not very soluble, and therefore are preferably given in tablet form or as a suspension. Suitable methods of administering the compounds of the present invention and dosage forms can be found herein below.

The (5-aryl-1,2,4-thiadiazol)-3-yl thiourea derivatives or (5-aryl-1,2,4-thiadiazol)-3-yl urea derivatives of this invention can be administered as treatment for viral infections by any means that produces contact of the active agent with the agent's site of action in the body. They can be administered by any conventional means available for use in conjunction with pharmaceuticals, either as individual therapeutic agents or in a combination of therapeutic. Preferably the compounds of the present invention are administered as a pharmaceutical formulation comprising at least one compound of the present invention, as defined above, together with one or more pharmaceutically acceptable carriers. It can be co-administered in the form of a tablet or capsule, as an agglomerated powder or in a liquid form or as a liposome.

The compounds of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

The (5-aryl-1,2,4-thiadiazol)-3-yl thiourea derivatives or (5-aryl-1,2,4-thiadiazol)-3-yl urea derivatives of the present invention can also be coupled with soluble polymers as targetable drug carriers. Such polymers can include polyvinylpyrrolidone, pyran copolymer, polyhydroxylpropylmethacrylamide-phenol, polyhydroxyethylaspartamidephenol, or polyethyleneoxide-polylysine substituted with palmitoyl residues. Furthermore, the compounds of the present invention can be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

1. Combination Therapy

The compounds of the present invention may additionally be combined with other antiviral compounds to provide an operative combination. It is intended to include any chemically compatible combination of a compound of this inventive group with other compounds of the inventive group or other compounds outside of the inventive group, as long as the combination does not eliminate the antiviral activity of the compound of this inventive group. For example, one or more (5-aryl-1,2,4-thiadiazol)-3-yl thiourea derivatives or (5-aryl-1,2,4-thiadiazol)-3-yl urea derivatives can be combined with other antiviral agents or potentiators. Potentiators are materials which affect the body's response to the antiviral agent. In the case of HIV a combination therapy with AZT, TC-3 or protease inhibitors is effective. In the case of hepatitis, cyclovir, famciclovir or valacyclovir, Ribavirin, interferon or combinations of Ribavirin and Interferon or beta globulin is administered as a combination therapy. For herpes, a recombinant alpha interferon can be used as a combination therapy.

In some embodiments of the invention, a (5-aryl-1,2,4-thiadiazol)-3-yl thiourea derivatives or (5-aryl-1,2,4-thiadiazol)-3-yl urea derivatives is used in combination with one or more other therapeutic agents, such as anti-inflammatory, anti-viral, anti-fungal, amoebicidal, trichomonocidal, analgesic, anti-neoplastic, anti-hypertensives, anti-microbial and/or steroid drugs, to treat antiviral infections. In some preferred embodiments, viral infections are treated with a combination of one or more (5-aryl-1,2,4-thiadiazol)-3-yl thiourea derivatives or (5-aryl-1,2,4-thiadiazol)-3-yl urea derivatives with one or more of beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AZDU, delavirdine (Rescriptor™), rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof.

A "potentiator" can be any material which improves or increase the efficacy of the pharmaceutical composition or acts as an immunomodulator. One such potentiator is tripolidine and its cis-isomer which is used in combination with more (5-aryl-1,2,4-thiadiazol)-3-yl thiourea derivatives or (5-aryl-1,2,4-thiadiazol)-3-yl urea derivatives and optionally another therapeutic agent and or anti-viral agent. Tripolidine is described in U.S. Pat. No. 5,114,951 (1992). Another potentiator is procodazole, 1H-benzimidazole-2-propanoic acid; [β-(2-benzimidazole) propionic acid; 2-(2-carboxyethyl)benzimidazole; propazol]. Procodazole is a non-specific immunoprotective agent against viral and bacterial infections used with the compositions claimed herein. It is effective with one or more (5-aryl-1,2,4-thiadiazol)-3-yl thiourea derivatives or (5-aryl-1,2,4-thiadiazol)-3-yl urea derivatives in treating viral infections and can be combined with one or more other therapeutic agents.

The combination therapy can be sequential, that is the treatment with one agent first and then the second agent, or it can be treatment with both agents at the same time. The sequential therapy can be within a reasonable time after the completion of the first therapy before beginning the second therapy. The treatment with both agents at the same time can be in the same daily dose or in separate doses. For example treatment with one agent on day 1 and the other on day 2. The exact regimen will depend on the disease being treated, the severity of the infection and the response to the treatment.

2. Unit Dosage

The compounds of the present invention may administered in a unit dosage form and may be prepared by any methods well known in the art. Such methods include combining the compounds of the present invention with a carrier or diluent which constitutes one or more accessory ingredients. Typically, the formulations are prepared by uniformly mixing the active ingredient with liquid carriers or finely divided solid carriers or both, and then if necessary shaping the product. A pharmaceutical carrier is selected on the basis of the chosen route of administration and standard pharmaceutical practice. Each carrier must be "acceptable" In the sense of being compatible with the other ingredients of the formulation and not injurious to the subject. This carrier can be a solid or liquid and the type is generally chosen based on the type of administration being used. Examples of suitable solid carriers include lactose, sucrose, gelatin, agar and bulk powders. Examples of suitable liquid carriers include water, pharmaceutically acceptable fats and oils, alcohols or other organic solvents, including esters, emulsions, syrups or elixirs, suspensions, solutions and/or suspensions, and solution and or suspensions reconstituted from non-effervescent granules and effervescent preparations reconstituted from effervescent granules. Such liquid carriers may contain, for example, suitable solvents, preservatives, emulsifying agents, suspending agents, diluents, sweeteners, thickeners, and melting agents. Preferred carriers are edible oils, for example, corn or canola oils. Polyethylene glycols, e.g. PEG, are also good carriers.

Dosage forms (compositions suitable for administration) comprise from about 1 milligram to about 1000 milligrams of active ingredient per dosage unit. Preferably the dosage forms will contain from about 10 mg to about 500 mg. In these pharmaceutical compositions the active ingredient will ordinarily be present in an amount of about 0.5 to about 95% by weight based on the total weight of the dosage unit.

3. Pharmaceutical Kits

The present invention also includes pharmaceutical kits useful, for example, for the treatment of hepatitis infection, which comprise one or more containers containing a pharmaceutical composition comprising a therapeutically effective amount of a (5-aryl-1,2,4-thiadiazol)-3-yl thiourea derivatives or (5-aryl-1,2,4-thiadiazol)- 3-yl urea derivatives. Such kits can further include, if desired, one or more of various conventional pharmaceutical kit components, such as, for example, containers with one or more pharmaceutically acceptable carriers, additional containers, etc., as will be readily apparent to those skilled in the art. Printed instructions, either as inserts or as labels, indicating quantities of the components to be administered, guidelines for administration, and/or guidelines for mixing the components, can also be included in the kit. In the present disclosure it should be understood that the specified materials and conditions are important in practicing the invention but that unspecified materials and conditions are not excluded so long as they do not prevent the benefits of the invention from being realized.

Specific examples of pharmaceutical acceptable carriers and excipients that may be used to formulate oral dosage forms of the present invention are described in U.S. Pat. No. 3,903,297 to Robert, issued Sep. 2, 1975.

Techniques and compositions for making dosage forms useful in the present invention are described herein below.

Oral formulations suitable for use in the practice of the present invention include capsules, gels, cachets, tablets, effervescent or non-effervescent powders or tablets, powders or granules; as a solution or suspension in aqueous or non-aqueous liquid; or as an oil-in-water liquid emulsion or a water-in-oil emulsion. The compounds of the present invention may also be presented as a bolus, electuary or paste.

The formulations for oral administration may comprise a non-toxic, pharmaceutically acceptable, inert carrier such as lactose, starch, sucrose, glucose, methyl cellulose, magnesium stearate, dicalcium phosphate, calcium sulfate, mannitol, sorbitol, cyclodextrin and cyclodextrin derivatives and the like.

Capsule or tablets can be easily formulated and can be made easy to swallow or chew. Tablets may contain suitable binders, lubricants, diluents, disintegrating agents, coloring agents, flavoring agents, flow-inducing agents, and melting agents. A tablet may be made by compression or molding, optionally with one or more additional ingredients. Compressed tables may be prepared by compressing the active ingredient in a free flowing form (e.g., powder, granules) optionally mixed with a binder (e.g., gelatin, hydroxypropylmethlcellose), lubricant, inert diluent, preservative, disintegrant (e.g., sodium starch glycolate, cross-linked carboxymethyl cellulose) surface-active or dispersing agent. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like. Molded tablets may be made by molding in a suitable machine a mixture of the powdered active ingredient moistened with an inert liquid diluent.

The tablets may optionally be coated or scored and may be formulated so as to provide slow or controlled release of the active ingredient. Tablets may also optionally be provided with an enteric coating to provide release in parts of the gut other than the stomach.

Formulations suitable for topical administration in the mouth wherein the active ingredient is dissolved or suspended in a suitable carrier include lozenges which may comprise the active ingredient in a flavored carrier, usually sucrose and acacia or tragacanth; gelatin, glycerin, or sucrose and acacia; and mouthwashes comprising the active ingredient in a suitable liquid carrier.

Topical applications for administration according to the method of the present invention include ointments, cream, suspensions, lotions, powder, solutions, pastes, gels, spray, aerosol or oil. Alternately, a formulation may comprise a transdermal patch or dressing such as a bandage impregnated with an active ingredient and optionally one or more carriers or diluents. To be administered in the form of a transdermal delivery system, the dosage administration will, of course, be continuous rather than intermittent throughout the dosage regimen.

The topical formulations may desirably include a compound which enhances absorption or penetration of the active ingredient through the skin or other affected areas. Examples of such dermal penetration enhancers include dimethylsulfoxide and related analogues.

The oil phase of the emulsions of the composition used to treat subjects in the present invention may be constituted from known ingredients in a known manner. This phase may comprise one or more emulsifiers. For example, the oily phase comprises at least one emulsifier with a fat or an oil or with both a fat and an oil or a hydrophilic emulsifier is included together with a lipophilic emulsifier which acts as a stabilizer. Together, the emulsifier with or without stabilizer make up an emulsifying was, and the wax together with the oil and/or fat make up the emulsifying ointment base which forms the oily dispersed phase of the cream formulations.

Emulsifiers and emulsion stabilizers suitable for use in the formulation include Tween 60, Span 80, cetosteryl alcohol, myristyl alcohol, glyceryl monostearate and sodium lauryl sulphate, paraffin, straight or branched chain, mono-or dibasic alkyl esters, mineral oil. The choice of suitable oils or fats for the formulation is based on achieving the desired cosmetic properties, the properties required and compatibility with the active ingredient.

The compounds may also be administered vaginally for example, as pessaries, tampons, creams, gels, pastes, foams or spray formulations containing in addition to the active ingredient. Such carriers are known in the art.

Formulations for rectal administration may be presented as a suppository with a suitable base comprising, for example, cocoa butter or a salicylate.

Formulations suitable for nasal administration may be administered in a liquid form, for example, nasal spray, nasal drops, or by aerosol administration by nebulizer, including aqueous or oily solutions of the active ingredient. Formulations for nasal administration, wherein the carrier is a solid, include a coarse powder having a particle size, for example, of less than about 100 microns, preferably less than about 50 microns, which is administered in the manner in which snuff is taken, i.e., by rapid inhalation through the nasal passage from a container of the powder held close up to the nose.

Formulations suitable for parenteral administration include aqueous and non-aqueous isotonic with the blood of the intended recipient; and aqueous and non-aqueous sterile suspensions which may include suspending systems which are designed to target the compound to blood components or one or more organs. The formulations may be presented in unit-dose or multi-dose sealed containers, for example, ampoules and vials. Extemporaneous injections solutions and suspensions may be prepared from sterile powders, granules and tablets of the kind previously described.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

Intravenously, the most preferred doses can range from about 1 to about 10 mg/kg/minute during a constant rate infusion. (5-Aryl-1,2,4-thiadiazol)-3-yl derivatives or (5-aryl-1,2,4-thiadiazol)-3-yl urea derivatives can be administered in a single daily dose, or the total daily dosage can be administered in divided doses of two, three, or four times daily. The (5-aryl-1,2,4-thiadiazol)-3-yl- derivatives or (5-aryl-1,2,4-thiadiazol)-3-yl urea derivatives can be given in one or more doses on a daily basis or from one to three times a week.

The present invention additionally include administering compounds of the herein described formula for the use in the form of veterinary formulations, which may be prepared, for example, by methods that are conventional in the art.

Useful pharmaceutical dosage forms for administration of the compounds of this invention are illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings can be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Liposomes can also be used for injectable compositions.

Suspension

An aqueous suspension is prepared for oral administration so that each 5 ml contain 100 mg of finely divided active ingredient, 200 mg of sodium carboxymethyl cellulose, 5 mg of sodium benzoate, 1.0 g of sorbitol solution, U.S.P., and 0.025 ml of vanillin.

G. Method of Treatment

The method of treatment can be any suitable method which is effective in the treatment of the particular virus or viral infection that is being treated. Treatment includes administering a therapeutically effective amount of the compounds of the present invention in a form described herein above, to a subject in need of treatment. As previously described, the composition can be administered oral, rectal, topical, vaginally, nasally, parenterally, intravenously and the like. The method of applying an effective amount varies depending on the viral infection being treated and the desired blood level. It is believed that parenteral treatment by intravenous, subcutaneous, or intramuscular application of (5-aryl-1,2,4-thiadiazol)-3-yl thiourea derivatives or (5-aryl-1,2,4-thiadiazol)-3-yl urea derivatives, formulated with an appropriate carrier, additional viral inhibiting compound or compounds or diluent to facilitate application will be the preferred method of administering the compounds to mammals or warm blooded animals.

H. Test Methods

The Protease Inhibition Assay

Protease inhibition is evaluated using a fluorometric method. Enzyme (Bachem) is diluted to 116 $\mu$gm/ml in 50 mM NaOAC, 5 mM DTT, 2 mM EDTA, 10% glycerol (pH 5.0) and stored as 10 $\mu$l samples at −20° C. HIV protease substrates I (Molecular Probes) are diluted to a working concentration of 0.32 nmoles/$\mu$l. Enzyme (20 $\mu$l) and drug (20 $\mu$l) are added to each well of a microtiter plate as appropriate. Positive and negative controls are evaluated in parallel. Fluorescence is quantitated on Labsystems Fluroskan II using 355 nm/460 nm at 37° C. at time zero and at 30 minute intervals for 2 hours. In instances where autofluorescence precludes use of the fluorometric, HIV-1 protease assay or confirmation of a result is required, an HPLC based protease assay can be employed.

Integrase Inhibition Assay

A biochemical integrase assay described by Craigie et at (HIV, vol. 2: A practical Approach) Biochemistry, Molecular Biology and Drug Discovery, Ed. J. Karn 1995) to screen agents for their ability to inhibit HIV-1 integrase can be used. In this system, a kinased oligonucleotide serves as the target of 3' processing and the subsequent strand transfer reaction. The 3' processing reaction involves the removal of 2 nucleotides from the 3' ends of the substrate. This is followed by the strand transfer reaction in which the 3' ends are joined to the exposed 5' ends. The 20 $\mu$l reaction mixture contains 25 mM MOPS (pH 7.2), 100 g/ml BSA, 10 mM $\beta$mercaptoethanol, 10% glycerol, 7.5 mM $MnCl_2$, 25 nM (7 ng) substrate (Oligo's Etc., Wilsonville, Oreg.) and 200 nM (128 ng) integrase (NIAID AIDS Research and Reference Reagent Program, Bethesda, Md.). The reaction proceeds at 37° C. for 1–2 hours and is terminated by the addition of 20 $\mu$l of sequencing stop solution (USB Amersham, Arlington Heights, Ill.). The reaction products are visualized by autoradiography following electrophoresis in 15% polyacrylamide 6 M Urea gel. The substrate migrates as a 30 mer, the product of 3' processing migrates as an N-2 band and the strand transfer products migrate more slowly at various sizes larger than the substrate.

Toxicity Values

Toxicity quantification involves the XTT-based evaluation. Assays were designed to characterize the long term effects of the compounds on virus production and to characterize the longer term effects of the compounds on virus production from chronically HIV infected cells.

CEM-SS cells chronically infected with HIV isolate, for example SKI (CEM-SKI) are cultured in RPM11640 tissue culture medium supplemented with 10% fetal bovine serum and antibiotics. Selection is performed by culturing the cells in the presence of the compound to be tested in T25 flasks. CEM-SKI or other infected cells with no added drug are used as the control cells.

Cells are allowed to grow to a density of approximately 1×106 cells/ml and are then passaged at a 1:10 dilution. After a period of time, usually one week intervals of drug treatment, cells are evaluated to determine if the inhibitory activity of the compound has been affected by treatment of the cells with either compound. The drug concentration in the flask is then increased two-fold and the cells maintained as above.

The cell populations contain integrated copies of the HIV genome and constitutively produce HIV at relatively high levels or are latently infected and only produce virus after stimulation with phorbol esters, tumor necrosis factor or IL6(U1 and ACH2). Reductions in virus products were observed when quantifying supernatant reverse transcriptase activity.

Reverse Transcriptase Inhibition Assay

A recombinant, purified HIV-1 reverse transcriptase (RT) enzyme provided by Dr. Steven Hughes (ABL,NCI-FCRDC) is used. Characterization of the RT inhibitory properties of selected test compounds is performed utilizing a RT assay described by Boyer et al (1993) with minor modifications. Briefly recombinant RT enzymes are assayed in microtiter plates in a 100 ml reaction mixture containing 25mM Tris-HCl, pH 8.0, 75 mM KCL, 8 mM $MgCl_2$, 2 mM DTT, 10 mMdGTP, 0.01 U rC:dG template (Pharmacia), 10 mCi [$P^{32}$]-a-dGTP (800 Ci/mmol), and the test compound at indicated concentrations.

The RT enzyme concentration employed in these assays ranged from 0.4–0.9 mgm/ml for the different recombinant proteins; all the RT enzymes reactions are allowed to proceed for 30 min at 37° C. before termination of the enzyme reaction by addition of 10% TCA; 100-mg of heat-denatured, sonicated salmon sperm DNA is also added to aid DNA precipitation and recovery.

Upon termination of the enzyme reaction, the TCA precipitated DNA is harvested onto glass fiber filters (GF/C), washed twice with ice-cold 10% TCA and subjected to liquid scintillation counting. To increase sample throughput and minimize sample handling of this assay, a 96 well glass fiber filter plate and vacuum manifold (Millpore) is used to harvest and wash the DNA.

The labeled DNA samples are subsequently counted directly in the multi-well plate by addition of 20 ml scintillation fluid (OptiPhase Super Mix, Wallac) to each well and using a MicroBeta 96 well scintillation counter (Wallac)

EXAMPLE 1

Mechanism

The mechanism of action of the (5-aryl-1,2,4-thiadiazol)-3-yl thiourea derivatives or (5-aryl-1,2,4-thiadiazol)-3-yl urea derivatives is not known. (5-phenyl-1,2,4-thiadiazol)-3-yl thiourea did not show activity as a protease inhibitor method or as an integrase inhibitor. The compound was screened using a fluorometric (protease inhibition assay) and autoradiography (integrase inhibition assay)

These results are summarized in the following tables:

| Protease Inhibition by 654021F-a known protease inhibitor | | | | | |
| --- | --- | --- | --- | --- | --- |
| Concentration (nM) | 0 | 1 | 10 | 100 | 1000 |
| % no drug control | 1000 | 99.0 | 99.7 | 91.3 | 29.3 |

| Protease Inhibition by (5-phenyl-1,2,4-thiadiazol)-3-yl thiourea | | | | | |
| --- | --- | --- | --- | --- | --- |
| Concentration (nM) | 0 | 1 | 10 | 100 | 1000 |
| % no drug control | 100.0 | 100.2 | 103.1 | 99.9 | 88.0 |

The $EC_{50}$ value is >100 μg/ml for (5-phenyl-1,2,4-thiadiazol)-3-yl thiourea and 0.699 μM/ml for 654021.

The results of the test using the compounds of the present invention are summarized as follows:

| HIV-1 Integrase Inhibition by (5-phenyl-1,2,4-thiadiazol)-3-yl thiourea | | | | | |
| --- | --- | --- | --- | --- | --- |
| Concentration (μg/ml) | 0 | 0.1 | 1 | 10 | 100 |
| % no drug control | 100.0 | 98.8 | 107.8 | 116.8 | 106.1 |

| HIV-1 Integrase Inhibition by TPX-a known integrase inhibitor | | | | |
| --- | --- | --- | --- | --- |
| Concentration (μM) | 0 | 0.1 | 1 | 10 |
| % no drug control | 100.0 | 86.1 | 26.8 | 31.2 |

The $EC_{50}$ value is 0.648 μM for TPX and >100 μg/ml for (5-phenyl-1,2,4-thiadiazol)-3-yl thiourea.

These tests demonstrate that the mechanism for the effective activity against HIV is not as a protease inhibitor or as an integrase inhibitor.

The following examples are illustrative and are not meant to be limiting to the invention.

EXAMPLE 2

BVDV Testing (5-Phenyl-1,2,4-thiadiazol)-3-yl thiourea was tested in vitro against BVDV at a dose range of 316 μg/ml to 0.01 μg/ml and compared to Ribavirin at 0.032 μM/ml to 10μM/ml. The solvent was DMSO (dimethylsulfoxide) and a control test of DMSO was screened at a dose range of 1% to 0.00316%. The Antiviral Index (AI) which is the $TC_5$/$IC_{50}$ is greater than 4000. A second screening test using (5-phenyl-1,2,4-thiadiazol)-3-yl thiourea had an AI of 1000.4. The AI for Ribavirin at 50% is 2.25. DMSO had no effect, as expected.

BVDV is a bovine diarrhea virus and is a well known surrogate virus for hepatitis C which cannot be cultured in vitro.

This test demonstrates the efficacy of (5-phenyl-1,2,4-thiadiazol)-3-yl thiourea in treating hepatitis C type viruses.

EXAMPLE 3

Herpes Simplex Testing (5-phenyl-1,2,4-thiadiazol)-3-yl thiourea was tested against HSV-2MS, a herpes simplex virus -2 in vero cells and compared with Acyclovir. The $IC_{50}$ for Acyclovir is 0.81 and 0.85 in a replicate study. The $TC_{50}$ is >1 and the TI or therapeutic index is >1.2. For (5-phenyl-1,2,4-thiadiazol)-3-yl thiourea the $IC_{50}$ is 159.6, the $TC_{50}$ is >200, the TI or therapeutic index is >1.3.

This test demonstrates that phenyl thiadiazolyl thiourea derivatives are effective in treating herpes simplex.

EXAMPLE 4

Kaposi's Sarcoma (5-phenyl-1,2,4-thiadiazol)-3-yl thiourea was tested against Kaposi's Sarcoma, a herpes virus, in vitro using the Human Herpes Virus 8(HHV8) cell line, TPA-induced BCBL-1 cells. The DNA copy number and the toxicity value were measured and compared with Cidofovir. Kaposi's sarcoma (KS) is a cancer that is often found in people with weak immune systems, such as those taking immunosuppressants or those with AIDS. The exact nature of the disease is uncertain, but it is almost always found in association with HHV8. Recent studies suggest that KS is caused by the herpes virus; that is, that KS is a herpes virus that manifests itself as a cancer.

Data for Cidofovir

| Conc. $\mu$M | 25 | 8 | 2.5 | 0.8 | 0.25 | 0.08 | 0 |
|---|---|---|---|---|---|---|---|
| DNA Copy Number (per 3 $\mu$l) | | | | | | | |
| sample 1 | 0 | 8.9 | 1329.8 | 7521 | 6668.9 | 8485.1 | 8855.9 |
| sample 2 | 0.0 | 0.0 | 1198.3 | 5985.4 | 6336.3 | 7948.1 | 9744.2 |
| sample 3 | 0.0 | 0.0 | 1275.7 | 1819.5 | 6995.5 | 9000.8 | 8075.7 |
| average | 0.0 | 3.0 | 1276.9 | 5108.6 | 6666.9 | 8478.0 | 8891.9 |
| % virus control | 0.0 | 0.0 | 14.3 | 57.5 | 75.0 | 95.3 | 100.0 |
| Toxicity Values | | | | | | | |
| sample 1 | 0.443 | 0.639 | 0.794 | 0.824 | 0.867 | 0.864 | 0.954 |
| sample 2 | 0.398 | 0.700 | 0.684 | 0.770 | 0.819 | 0.797 | 0.924 |
| sample 3 | 0.447 | 0.677 | 0.704 | 0.814 | 0.934 | 0.780 | 1.030 |
| average | 0.430 | 0.672 | 0.728 | 0.803 | 0.874 | 0.814 | 0.970 |
| % cell control | 44.0 | 69.3 | 75.0 | 82.8 | 90.1 | 83.9 | 100.0 |

$IC_{50}$ $\mu$M = 1.1
$TC_{50}$ $\mu$M = 21.1
TI = 19.2

Data for (5-phenyl-1,2,4-thiadiazol)-3-yl thiourea

| Conc. $\mu$M | 200 | 64 | 20 | 6.4 | 2 | 0.64 | 0 |
|---|---|---|---|---|---|---|---|
| Copy Number (per 3 $\mu$l) | | | | | | | |
| sample 1 | 489.6 | 149.8 | 747.8 | 1003.5 | 1100.2 | 1200.5 | 1657.8 |
| sample 2 | 163.7 | 1114.5 | 841.6 | 1084.5 | 1000.7 | 1258.4 | 1567.4 |
| sample 3 | 578.7 | 994.6 | 991.2 | 1009.7 | 1189.7 | 1198.4 | 1398.4 |
| average | 410.7 | 753.0 | 860.2 | 1032.6 | 1096.9 | 12198.1 | 1541.2 |
| % virus control | 26.6 | 48.9 | 55.8 | 67.0 | 71.2 | 79.1 | 100.0 |
| Toxicity Values | | | | | | | |
| sample 1 | 0.215 | 0.539 | 1.060 | 0.901 | 0.941 | 0.983 | 0.914 |
| sample 2 | 0.202 | 0.628 | 1.032 | 0.874 | 1.064 | 1.098 | 0.861 |
| sample 3 | 0.201 | 0.407 | 0.939 | 0.986 | 1.027 | 0.935 | 0.864 |
| average | 0.206 | 0.525 | 1.011 | 0.921 | 1.011 | 1.006 | 0.880 |
| % cell control | 23.4 | 59.7 | 114.8 | 104.6 | 114.9 | 114.3 | 100.0 |

$IC_{50}$ $\mu$M = 56.8
$TC_{50}$ $\mu$M = 100.3
TI = 1.8

This screening test demonstrates the effectiveness of (5-phenyl-1,2,4-thiadiazol)-3-yl thiourea against Kaposi's sarcoma, a herpes virus.

EXAMPLE 5

Hepatitis

In an in vitro virus production test of hepatitis B, HEPG2 2.2.15 the following results were obtained with (5-phenyl-1,2,4-thiadiazol)-3-yl thiourea.

| Conc. $\mu$g/ml | 200 | 64 | 20 | 6.4 | 2 | 0.64 | 0 |
|---|---|---|---|---|---|---|---|
| DNA Copy Number (per 3 $\mu$l) | | | | | | | |
| sample 1 | 61.5 | 98.6 | 49.1 | 180.2 | 149.3 | 131.5 | 271.2 |
| sample 2 | 20.5 | 76.0 | 54.6 | 46.7 | 20.3 | 155.2 | 244.0 |
| sample 3 | 97.9 | 87.8 | 22.0 | 59.4 | 83.4 | 150.8 | 278.4 |
| mean | 60.0 | 87.5 | 41.9 | 95.4 | 84.3 | 145.8 | 284.5 |
| % virus control | 22.7 | 33.1 | 15.8 | 36.1 | 31.9 | 55.1 | 100 |
| Toxicity Values | | | | | | | |
| sample 1 | 0.800 | 0.973 | 0.909 | 1.015 | 0.916 | 1.079 | 1.133 |
| sample 2 | 0.818 | 0.962 | 0.966 | 0.940 | 0.881 | 0.985 | 1.122 |
| sample 3 | 0.928 | 1.037 | 0.921 | 1.218 | 0.959 | 0.999 | 1.065 |
| mean | 0.849 | 0.991 | 0.932 | 1.058 | 0.919 | 1.021 | 1.107 |
| % cell control | 76.7 | 89.5 | 84.2 | 95.6 | 83.0 | 92.3 | 100.0 |

The $IC_{50}$ is 0.94 $\mu$g/ml; the $TC_{50}$ is >200 $\mu$g/ml and the therapeutic index or TI is 212.8.

In a replicate experiment, the $IC_{50}$ is 0.76 $\mu$g/ml; the $TC_{50}$ is >200 $\mu$g/ml, and the TI is 263.2.

For comparison 3TC was tested and the following data were obtained:

| Conc. $\mu$g/ml | 1 | 0.32 | 0.1 | 0.032 | 0.01 | 0.0032 | 0 |
|---|---|---|---|---|---|---|---|
| DNA Copy Number (per 3$\mu$l) | | | | | | | |
| sample 1 | 6.0 | 36.7 | 73.0 | 192.6 | 286.1 | 265.4 | 308.6 |
| sample 2 | 3.9 | 45.1 | 74.8 | 243.2 | 192.3 | 328.0 | 304.5 |
| sample 3 | 2.1 | 56.5 | 60.5 | 255.3 | 276.7 | 247.9 | 246.8 |

-continued

| Conc. µg/ml | 1 | 0.32 | 0.1 | 0.032 | 0.01 | 0.0032 | 0 |
|---|---|---|---|---|---|---|---|
| mean | 4.0 | 46.1 | 69.4 | 230.4 | 251.7 | 280.4 | 286.7 |
| % virus control | 1.4 | 13.1 | 24.2 | 80.4 | 87.8 | 97.8 | 100.0 |
| Toxicity Values | | | | | | | |
| sample 1 | 1.423 | 1.082 | 1.151 | 1.074 | 1.001 | 1.009 | 1.146 |
| sample 2 | 1.256 | 1.207 | 1.220 | 1.153 | 1.081 | 1.173 | 1.249 |
| sample 3 | 1.322 | 1.227 | 1.200 | 1.316 | 1.099 | 1.230 | 1.363 |
| mean | 1.334 | 1.172 | 1.190 | 1.181 | 1.060 | 1.137 | 1.253 |
| % cell control | 106.5 | 93.6 | 95.0 | 94.3 | 84.6 | 90.8 | 100.0 |

The $IC_{50}$ is 0.089 µg/ml; the $TC_{50}$ is >1 µg/ml and the TI is 14.6.

In a replicate experiment, the $IC_{50}$ is 0.021 pg/ml; the $TC_{50}$ is >1 µg/ml and the TI is >47.6.

(5-phenyl-1,2,4-thiadiazol)-3-yl thiourea can be used to treat hepatitis B.

EXAMPLE 6

CEMRF

A long term in vitro study of (5-phenyl-1,2,4-thiadiazol)-3-yl thiourea against an HIV-1 cell line, CEMRF was conducted at three different levels. The results with CEMRF cells was reported at weekly intervals. The data is summarized below.

| CEMRF cell line | | | | | | | | |
|---|---|---|---|---|---|---|---|---|
| Day | 4 | 11 | 18 | 25 | 32 | 39 | 46 | 53 |
| No Drug | 4338 | 2847 | 3216 | 3843 | 2924 | 3084 | 2815 | 2113 |
| 7 µg/ml | 5423 | 2249 | 2951 | 3606 | 2655 | 2570 | 2952 | 2241 |
| 15 µg/ml | 6226 | 2530 | 3842 | 2647 | 2128 | 2104 | 1843 | 1958 |
| 30 µg/ml | 4659 | 1767 | 2369 | 1847 | 2008 | 659 | 924 | 1438 |

The CEMRF is a viral strain of the CEMSS cell line. This test demonstrates the effectiveness of (5-phenyl-1,2,4-thiadiazol)-3-yl thiourea in treating HIV-1.

EXAMPLE 7

CEMIIIB

A long term in vitro study of (5-phenyl-1,2,4-thiadiazol)-3-yl thiourea against an HIV-1 cell line, CEMIIIB was conducted at three different levels. The results with CEMIIIB cells was reported at weekly intervals. The data is summarized below.

| CEMIIIB | | | | | | | | |
|---|---|---|---|---|---|---|---|---|
| Day | 4 | 11 | 18 | 25 | 32 | 39 | 46 | 53 |
| No Drug | 5665 | 7735 | 7184 | 5010 | 5452 | 7382 | 11423 | 11781 |
| 7 µg/ml | 4849 | 6658 | 7078 | 5221 | 5329 | 7349 | 11262 | 11286 |

-continued

| CEMIIIB | | | | | | | | |
|---|---|---|---|---|---|---|---|---|
| Day | 4 | 11 | 18 | 25 | 32 | 39 | 46 | 53 |
| 15 µg/ml | 5078 | 5733 | 6057 | 4980 | 4273 | 6329 | 10361 | 9844 |
| 30 µg/ml | 5251 | 6200 | 6952 | 4110 | 3337 | 4233 | 9238 | 3527 |

The CEMIIIB is a viral strain of the CEMSS cell line.

EXAMPLE 8

CEMROD

A long term in vitro study of (5-phenyl-1,2,4-thiadiazol)-3-yl thiourea against an HIV-2 cell line, CEMROD was conducted at three different levels. The results with CEMROD cells was reported at weekly intervals. The data is summarized below.

| CEMROD | | | | | | | | |
|---|---|---|---|---|---|---|---|---|
| Day | 4 | 11 | 18 | 25 | 32 | 39 | 46 | 53 |
| No Drug | 7041 | 9468 | 11612 | 8853 | 8795 | 6947 | 8270 | 7233 |
| 7 µg/ml | 6593 | 8676 | 10912 | 9356 | 8803 | 6655 | 8280 | 7549 |
| 15 µg/ml | 6815 | 8202 | 10389 | 7816 | 6672 | 7087 | 6457 | 6544 |
| 30 µg/ml | 6626 | 6582 | 7494 | 4421 | 4056 | 2118 | 4117 | 4779 |

The CEMROD cell line is a viral strain of the CEMSS cell line.

EXAMPLE 9

U937IIIB

A long term in vitro study of (5-phenyl-1,2,4-thiadiazol)-3-yl thiourea against an HIV-1 cell line, U937IIIB was conducted at three different levels. The results with U937IIIB cells were reported at weekly intervals. The data is summarized below.

| Day | 4 | 11 | 18 | 25 | 32 | 39 | 46 | 53 |
|---|---|---|---|---|---|---|---|---|
| No Drug | 13419 | 11165 | 8246 | 6241 | 3286 | 5858 | 3861 | 4946 |
| 7 µg/ml | 9368 | 8889 | 7566 | 5781 | 3414 | 5346 | 4085 | 4832 |
| 15 µg/ml | 9710 | 8025 | 5435 | 6064 | 2479 | 4377 | 3867 | 3510 |
| 30 pg/ml | 9549 | 7639 | 3551 | 4611 | 1855 | 2410 | 1550 | 1819 |

The U937IIIB cell line is viral strain of the U937 cell line.

EXAMPLE 10

U937RF

A long term in vitro study of (5-phenyl-1,2,4-thiadiazol)-3-yl thiourea against U937RF, a protease resistant strain, was conducted at three different levels. The results with U937RF cells were reported at weekly intervals. The data is summarized below.

| Day | 4 | 11 | 18 | 25 | 32 | 39 | 46 | 53 |
|---|---|---|---|---|---|---|---|---|
| No Drug | 1522 | 1787 | 4849 | 6943 | 4331 | 5982 | 3061 | 5665 |
| 7 μg/ml | 1627 | 1526 | 4086 | 5303 | 4827 | 6008 | 3586 | 5726 |
| 15 μg/ml | 1575 | 1482 | 3772 | 2654 | 1594 | 3538 | 2426 | 3976 |
| 30 ρg/ml | 1751 | 1237 | 2892 | 735 | 1035 | 1265 | 1358 | 2333 |

EXAMPLE 11

Protease Resistant HIV Strains

A long term in vitro study of (5-phenyl-1,2,4-thiadiazol)-3-yl thiourea against U937JE225R, a protease resistant strain, was conducted at three different levels. The results with U937JE225R cells was reported at weekly intervals. The data is summarized below.

| Day | 4 | 11 | 18 | 25 | 32 | 39 | 46 | 53 |
|---|---|---|---|---|---|---|---|---|
| No Drug | 17369 | 13829 | 12419 | 10076 | 6887 | 11668 | 10289 | 10655 |
| 7 μg/ml | 12165 | 9465 | 10341 | 9079 | 6797 | 9792 | 9915 | 1094 |
| 15 μg/ml | 11151 | 9935 | 9738 | 7104 | 6426 | 10618 | 10471 | 9756 |
| 30 ρg/ml | 12033 | 9859 | 11874 | 5281 | 4154 | 5379 | 5239 | 4423 |

Similar results are obtained with U937KN1272, a protease resistant strain, reported below.

| Day | 4 | 11 | 18 | 25 | 32 | 39 | 46 | 53 |
|---|---|---|---|---|---|---|---|---|
| No Drug | 105239 | 80338 | 72031 | 62080 | 29644 | 46674 | 28686 | 35449 |
| 7 μg/ml | 119839 | 78089 | 74773 | 78997 | 31156 | 41326 | 31024 | 31209 |
| 15 μg/ml | 103341 | 80161 | 73939 | 74262 | 26305 | 28635 | 18073 | 22110 |
| 30 ρg/ml | 114070 | 89087 | 72398 | 38006 | 6908 | 14779 | 5663 | 10534 |

EXAMPLE 12

HIV-2

An in vitro screening test of (5-phenyl-1,2,4-thiadiazol)-3-yl thiourea against an HIV-2 virus, CEMROD was performed.

The results of one test are shown below

| Conc. μg/ml | 0 | 0.32 | 1 | 3.2 | 1.0 | 32 | 100 |
|---|---|---|---|---|---|---|---|
| Reverse Transcriptase Activity | | | | | | | |
| sample 1 | 4752 | 4664 | 4005 | 4166 | 3001 | 1832 | 72 |
| sample 2 | 4989 | 6972 | 4407 | 3318 | 3077 | 1550 | 48 |
| sample 3 | 4709 | 4717 | 5392 | 3334 | 3547 | 1876 | 52 |
| average | 4817 | 5451 | 4601 | 3606 | 3208 | 1753 | 57 |
| % virus control | 100 | 113.2 | 95.5 | 74.9 | 66.6 | 36.4 | 1.2 |
| Toxicity Values | | | | | | | |
| sample 1 | 1.1039 | 1.181 | 1.055 | 0.987 | 0.871 | 0.518 | 0.113 |
| sample 2 | 1.193 | 1.206 | 1.093 | 0.984 | 0.881 | 0.491 | 0.117 |
| sample 3 | 1.202 | 1.203 | 1.066 | 0.965 | 0.921 | 0.517 | 0.115 |
| average | 1.178 | 1.197 | 1.071 | 0.979 | 0.891 | 0.509 | 0.115 |

-continued

| Conc. μg/ml | 0 | 0.32 | 1 | 3.2 | 1.0 | 32 | 100 |
|---|---|---|---|---|---|---|---|
| % cell control | 100 | 101.6 | 90.9 | 83.1 | 75.6 | 43.2 | 9.8 |

EXAMPLE 13

HIV-1

A long term in vitro study of (5-phenyl-1,2,4-thiadiazol)-3-yl thiourea against an HIV-1 cell line, CEMSKI was conducted at three different levels. The results with CEMSKI cells was reported at weekly intervals. The data is summarized below.

| CEMSKI cell line | | | | | | | | |
|---|---|---|---|---|---|---|---|---|
| Day | 4 | 11 | 18 | 25 | 32 | 39 | 46 | 53 |
| No Drug | 7041 | 9468 | 11612 | 8853 | 8795 | 6947 | 8270 | 7233 |
| 7 μg/ml | 6593 | 8676 | 10912 | 9356 | 8803 | 6655 | 8280 | 7549 |
| 15 μg/ml | 6815 | 8202 | 10389 | 7816 | 6672 | 7087 | 6457 | 6544 |
| 30 ρg/ml | 6626 | 6582 | 7494 | 4421 | 4056 | 2118 | 4117 | 4779 |

This test was repeated and similar results were obtained:

| CEMSKI cell line | | | | | | | | |
|---|---|---|---|---|---|---|---|---|
| Day | 4 | 11 | 18 | 25 | 32 | 39 | 46 | 53 |
| No Drug | 7036 | 7735 | 8174 | 4516 | 3213 | 9070 | 14059 | 12904 |
| 7 μg/ml | 6224 | 6658 | 7207 | 5725 | 3161 | 9602 | 13984 | 11578 |
| 15 μg/ml | 5685 | 5733 | 6236 | 3752 | 2451 | 5526 | 12397 | 9662 |
| 30 ρg/ml | 4789 | 5200 | 4821 | 2418 | 1651 | 3386 | 9353 | 6466 |

The CEMSKI cell like is a viral strain of the CEMSS cell line.

EXAMPLE 14

Anti-Fungal Activity (5-phenyl-1,2,4-thiadiazol)-3-yl thiourea was tested against a number of fungi in vitro. It was active against *Cryptococcus neoformans* and *curvularai lunata*. The cidal activity for the *C. neoformans* is high enough that it is clear static against this yeast. This test was conducted using a method based upon NCCLS reference method M-27A published in 1997. Solvent, medium and growth controls were set-up with the tests. Once these were read to validate the test performance, the QC fungi were read to insure they had expected results. These steps validated the test system. DMSO was used as a drug-chemical solvent. These test were read following incubation at 35° C. when the QC organisms (Candida spp.) showed good growth. MIC values were concentration in which growth was inhibited or reduced at least 90% in comparison to the control growth. The 90% cut-off is necessary for azoles, which are static and not cidal. The FMC or cidal level, was determined by sub-culturing a sample form each tube showing no growth.

*Curvularia lunata* causes mycotic keratitis, sinus and deep organ infections. It is opportunistic in immunocompromised patients.

*Cryptococcus neoformans* is an opportunistic pathogen involving the central nervous system in AIDS. It is a yeast having protective polysaccharide capsule that is a basidiomycete.

The abbreviations used for the compounds are:

AmB is amphotericin B

Thia is thiabendazole

Methyl is methyl 1,2-benzmimidazole carbamate or benomyl

Itra is Itraconazole

Phth is (5-phenyl-1,2,4-thiadiazol)-3-yl thiourea

| Phth | AmB | Thia | Methyl | Itra |
|------|------|------|--------|------|
| MIC data (µg/ml) *Curvularia lunata* | | | | |
| 0.03 | 0.06 | 0.032 | 0.03 | 0.03 |
| MIC data (µg/ml) *Cryptococcus neoformans* | | | | |
| 32 | 0.125 | 32 | 8 | 0.03 |
| MFC data (µg/ml) *Cryptococcus neoformans* | | | | |
| 32 | 0.5 | 32 | 32 | 32 |
| MFC data (µg/ml) *Curvularia lunata* | | | | |
| 0.03 | 0.125 | 32 | 32 | 0.06 |

(5-phenyl-1,2,4-thiadiazol)-3-yl thiourea is effective against these two fungi which are commonly found in AIDS patients. These phenyl thiadiazolyl derivatives can be used to treat HIV and to prevent the development of secondary fungal infections.

What is claimed is:

1. A method of treating a viral infection comprising administering to a patient in need thereof a therapeutically effective amount of a (5-aryl-1,2,4-thiadiazol)-3-yl thiourea derivative or a (5-aryl-1,2,4-thiadiazol)-3-yl urea derivative having the formula:

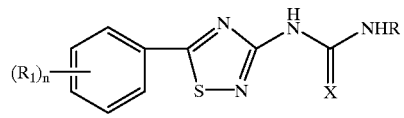

wherein,

X is oxygen or sulfur;

R is hydrogen or alkyl having from 1 to 3 carbon atoms;

n is 0–4; and $R_1$ is hydrogen, alkyl having from 1 to 7 carbon atoms, chloro, bromo, fluoro, oxychloro, or alkoxy having the formula —O(CH$_2$($_y$CH$_3$ wherein y is from 1 to 6.

2. A method according to claim 1 wherein said (5-aryl-1,2,4-thiadiazol)-3-yl thiourea derivative or (5-aryl-1,2,4-thiadiazol)-3-yl urea derivative is in the form of a pharmaceutical addition salt thereof.

3. A method according to claim 2 wherein said pharmaceutical addition salt is a chloride salt.

4. A method according to claim 1 wherein said (5-aryl-1,2,4-thiadiazol)-3-yl thiourea derivative or (5-aryl-1,2,4-thiadiazol)-3-yl urea derivative is in the form of a prodrug thereof.

5. A method according to claim 1 wherein said viral infection is selected from the group consisting of HIV, herpes simplex, hepatitis, and HHV8.

6. A method according to claim 5 wherein said viral infection is hepatitis C or hepatitis B.

7. A method according to claim 5 wherein said viral infection is HIV.

8. A method according to claim 5 wherein said (5-aryl-1,2,4-thiadiazol)-3-yl thiourea derivative or (5-aryl-1,2,4-thiadiazol)-3-yl urea derivative is in the form of a pharmaceutical addition salt thereof.

9. A method according to claim 5 wherein said (5-aryl-1,2,4-thiadiazol)-3-yl thiourea derivative or a (5-aryl-1,2,4-thiadiazol)-3-yl urea derivative is in the form of a prodrug thereof.

10. A method according to claim 1 wherein said method comprises administering to a patient in need thereof from about 1 mg/kg body weight to about 10,000 mg/kg body weight of said (5-aryl-1,2,4-thiadiazol)-3-yl thiourea derivative or (5-aryl-1,2,4-thiadiazol)3-yl urea derivative.

11. A method according to claim 1 wherein said method comprises administering a therapeutic agent in a combination therapy with said (5-aryl-1,2,4-thiadiazol)-3-yl thiourea derivative or (5-aryl-1,2,4-thiadiazol)-3-yl urea derivative.

12. A method according to claim 11 wherein said therapeutic agent is selected from the group consisting of AZT, TC-3, protease inhibitors, acyclovir, famiciclovir, valacyclovir, Ribavirin, interferon, a combination of Ribavirin and interferon, a combination of Ribavirin and beta globulin, a recombinant alpha interferon, and mixtures thereof.

13. A method according to claim 1 wherein said (5-aryl-1,2,4-thiadiazol)-3-yl thiourea derivative or (5-aryl-1,2,4-thiadiazol)-3-yl urea derivative is administered in a solid form and wherein said solid form includes a carrier selected from the group consisting of lactose, sucrose, gelatin and agar.

14. A method according to claim 1 wherein said (5-aryl-1,2,4-thiadiazol)-3-yl thiourea derivative or (5-aryl-1,2,4-thiadiazol)-3-yl urea derivative is administered in a liquid form and wherein said liquid form is selected from the group consisting of an aqueous solution, an alcohol solution, an emulsion, a suspension reconstituted from non-effervescent or effervescent preparations, and a suspension in pharmaceutically acceptable fats or oils.

15. A method according to claim 1 wherein said 5-aryl-1,2,4-thiadiazol)-3-yl thiourea derivative has the formula:

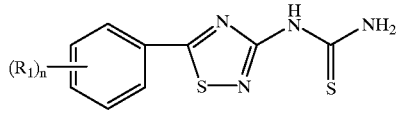

wherein n is 0–4, and $R_1$ is hydrogen or alkyl having from 1 to 7 carbon; or a pharmaceutical addition salt thereof.

16. A method of treating a viral infection comprising administering to a patient in need thereof a therapeutically effective amount of (5-phenyl-1,2,4-thiadiazol)-3-yl thiourea, which has the formula:

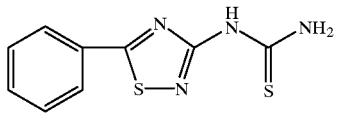

or a pharmaceutical addition salt thereof.

17. A method according to claim 16 wherein said (5-phenyl-1,2,4-thiadiazol)-3-yl thiourea is in the form of a prodrug thereof.

18. A method according to claim 16 wherein said viral infection is selected from the group consisting of HIV, herpes simplex, hepatitis, and HHV8.

19. A method according to claim 16 wherein said method comprises administering to a patient in need thereof from about 1 mg/kg body weight to about 10,000 mg/kg body weight of said (5-phenyl-1,2,4-thiadiazol)-3-yl thiourea.

20. A method according to claim 16 wherein said treatment comprises administering a therapeutic agent in a combination therapy with said (5-phenyl-1,2,4-thiadiazol)-3-yl thiourea.

21. A method according to claim 20 wherein said therapeutic agent is selected from the group consisting of AZT, TC-3, protease inhibitors, acyclovir, famiciclovir, valacyclovir, Ribavirin, interferon, a combination of Ribavirin and interferon, a combination of Ribavirin and beta globulin, a recombinant alpha interferon, and mixtures thereof.

22. A method according to claim 16 wherein said viral infection is hepatitis C or hepatitis B or herpes simplex or HIV.

23. A method of treating a fungal infection comprising administering to a subject in need thereof a pharmaceutical composition comprising a therapeutically effective amount of a (5-aryl-1,2,4-thiadiazol)3-yl thiourea derivative or a (5-aryl-1,2,4thiadiazol)-3-yl urea derivative having the formula:

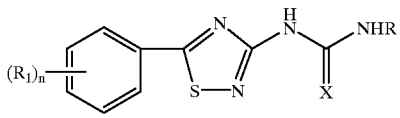

wherein,
X is oxygen or sulfur;
R is hydrogen or alkyl having from 1 to 3 carbon atoms;
n is 0–4; and
$R_1$ is hydrogen, alkyl having from 1 to 7 carbon atoms, chloro, bromo, fluoro, oxychloro, or alkoxy having the formula —O(CH$_2$)$_y$CH$_3$ wherein y is from 1 to 6.

24. A method according to claim 23 wherein said (5-aryl-1,2,4-thiadiazol)-3-yl thiourea derivative or (5-aryl-1,2,4-thiadiazol)-3-yl urea derivative is in the form of a pharmaceutical addition salt thereof.

25. A method according to claim 23 wherein said (5-aryl-1,2,4-thiadiazol)3-yl thiourea derivative or (5-aryl-1,2,4-thiadiazol)-3-yl urea derivative is in the form of a prodrug thereof.

26. A method according to claim 23 wherein said (5-aryl-1,2,4-thiadiazol)3-yl thiourea derivative has the formula:

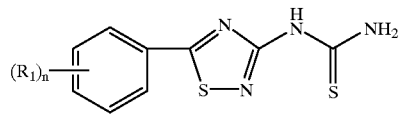

wherein n is 0–4, and $R_1$ is hydrogen or alkyl having from 1 to 7 carbon; or a pharmaceutical addition salt thereof.

27. A method according to claim 26 wherein n is 4 and $R_1$ is hydrogen.

28. A method of treating bovine diarrhea viral infection comprising administering to a patient in need thereof a therapeutically effective amount of a (5-aryl-1,2,4-thiadiazol)-3-yl thiourea derivative or a (5-aryl-1,2,4-thiadiazol)-3-yl urea derivative having the formula:

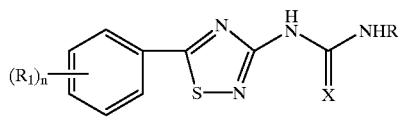

wherein,
X is oxygen or sulfur;
R is hydrogen or alkyl having from 1 to 3 carbon atoms;
n is 0–4; and
$R_1$ is selected from the group consisting of hydrogen, alkyl having from 1 to 7 carbon atoms, chloro, bromo, fluoro, oxychloro, or alkoxy having the formula —O(CH$_2$)$_y$CH$_3$ wherein y is from 1 to 6.

29. A method according to claim 28 wherein said (5-aryl-1,2,4-thiadiazol)-3-yl thiourea derivative or (5-aryl-1,2,4-thiadiazol)3-yl urea derivative is in the form of a pharmaceutical addition salt thereof.

30. A method according to claim 28 wherein said (5-aryl-1,2,4-thiadiazol)3-yl thiourea derivative or (5-aryl-1,2,4-thiadiazol)-3-yl urea derivative is in the form of a prodrug thereof.

31. A method according to claim 28 wherein said (5-aryl-1,2,4-thiadiazol)-3-yl thiourea derivative has the formula:

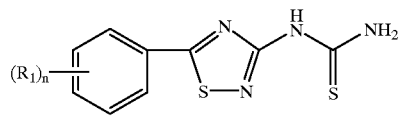

wherein n is 0–4, and $R_1$ is hydrogen or alkyl having from 1 to 7 carbon; or a pharmaceutical addition salt thereof.

32. A method according to claim 31 wherein n is 4 and $R_1$ is hydrogen.

* * * * *

UNITED STATES PATENT AND TRADEMARK OFFICE
CERTIFICATE OF CORRECTION

PATENT NO. : 6,258,831 B1
DATED : July 10, 2001
INVENTOR(S) : James Berger Camden It is certified that error appears in the above-identified patent and that said Letters Patent is hereby corrected as shown below:

Column 22, claim 1,
Line 15, delete the second occurrence of "(" and insert in lieu thereof -- ) --.

Column 22, claim 10,
Line 43, immediately after ')', insert -- - --.

Column 22, claim 12,
Line 50, delete "famiciclovir" and insert in lieu thereof -- famciclovir --.

Column 23, claim 15,
Line 1, immediately before '5' insert -- ( --.

Column 23, claim 21,
Line 38, delete "famiciclovir" and insert on lieu thereof -- famclovir --.

Column 23, claim 23,
Line 48, immediately after ')', insert -- - --.
Line 49, immediately after '4' insert -- - --.

Column 24, claim 25,
Line 6, immediately after ')', insert -- - --.

Column 24, claim 26,
Line 9, immediately after ')', insert -- - --.

Column 24, claim 29,
Line 44, immediately after ')', insert -- - --.

UNITED STATES PATENT AND TRADEMARK OFFICE
CERTIFICATE OF CORRECTION

PATENT NO. : 6,258,831 B1
DATED : July 10, 2001
INVENTOR(S) : James Berger Camden It is certified that error appears in the above-identified patent and that said Letters Patent is hereby corrected as shown below:

Column 24, claim 30,
Line 47, immediately after ')', insert -- - --.

Signed and Sealed this

Twelfth Day of March, 2002

Attest:

Attesting Officer

JAMES E. ROGAN
Director of the United States Patent and Trademark Office